United States Patent [19]

Ohta et al.

[11] Patent Number: 5,405,314

[45] Date of Patent: Apr. 11, 1995

[54] WOUND PROTECTING MEMBER INCLUDING CHITIN

[75] Inventors: Hisato Ohta, Tottori; Kazuki Takaishi; Noriko Uetani, both of Osaka, all of Japan

[73] Assignees: Sunfive Company Ltd., Tottori; Kanae Company Ltd., Osaka, both of Japan

[21] Appl. No.: 141,282

[22] Filed: Oct. 22, 1993

[30] Foreign Application Priority Data

| Nov. 2, 1992 [JP] | Japan | 4-317712 |
| Nov. 2, 1992 [JP] | Japan | 4-317800 |
| Nov. 5, 1992 [JP] | Japan | 4-352777 |
| Nov. 5, 1992 [JP] | Japan | 4-352778 |

[51] Int. Cl.⁶ .................. A61F 13/00; A61F 15/00
[52] U.S. Cl. .................. 602/49; 602/42; 602/48; 604/307
[58] Field of Search .................. 602/42, 48, 49; 604/304, 307

[56] References Cited

U.S. PATENT DOCUMENTS

| 3,903,268 | 9/1975 | Balassa | 602/49 |
| 4,360,015 | 11/1982 | Mayer | 602/42 |
| 4,651,725 | 3/1987 | Kifune et al. | 602/48 |
| 4,685,907 | 8/1987 | Argen et al. | 602/48 |
| 4,956,350 | 9/1990 | Mosbey | 514/55 |
| 5,116,824 | 5/1992 | Miyata et al. | 514/55 |

FOREIGN PATENT DOCUMENTS 2274257  11/1990  Japan .................. 602/49

*Primary Examiner*—Paul Prebilic
*Attorney, Agent, or Firm*—Koda and Androlia

[57] ABSTRACT

A member for protecting a wound surface including a film of a water soluble polymer, a powdered chitin coated on the film, a body fluid absorbing layer, such as, compressed cotton, cellulose sponge and non-woven textured fabric provided on the back surface of the film and a tape material adhered to the body fluid absorbing layer by an adhesive.

4 Claims, 3 Drawing Sheets

WOUND PROTECTING MEMBER INCLUDING CHITIN

BACKGROUND OF THE INVENTION

1. Field of the Invention

The present invention relates to a wound protecting material which remarkably improves a defect in conventional wound protecting materials by using a chitin powder together with a water soluble polymer film which is dissolvable by blood.

2. Prior Art

Many materials are produced on a commercial scale, used and proposed as a protective material for applying to a wound surface. However, such conventional materials are made from cloth or a film. As a result, tearing them off from a wound surface is very difficult due to the combining with the granulation tissue after being used for a comparatively long time. Therefore, if torn off, the wound surface undergoes a bad effect.

Furthermore, wound surface protective materials in which chitin is used are suggested in Japanese Patent Application No. 60-85169 and 60-23608 (Publication No. 62-97557), and these patents suggest that chitin has the effect of stopping blood. Chitin is a type of amino sugar polymer and is included in the shells of insects, crustaceans and mollusks and further in the shells of the eggs of animals and birds. However, these conventional wound protective materials are made from forming the chitin into a fiber form in which the pore volume corresponds to an ooze-out liquid volume from a wound surface. As a result, it has high adhesivity to the wound surface and can be naturally torn in the case of long term use; however, it has the disadvantage that tearing off causes pain and that the wound surface is made worse by the adhesivity to the wound in the case of short term uses as a first aid plaster.

SUMMARY OF THE INVENTION

The object of the present invention is to provide a wound surface protective material in which the wound treatment blood stopping effect are exhibited during application to the wound surface and only chitin remains on the wound surface when the material is torn off without causing pain or aggravation to the wound.

DETAILED DESCRIPTION OF THE INVENTION

Figure 1:
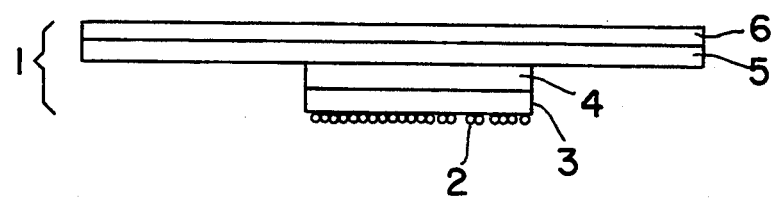
FIG. 1 is an enlarged sectional view of a first embodiment of a wound surface protective material according to the present invention.

The applying material of the present invention is made of a film on which powdered chitin is coated, or a film formed from a dispersion liquid including powdered chitin or a net upon which the powdered chitin is adhered.

The invention is explained in detail based upon the following embodiments as is shown in the drawings.

Embodiment 1

FIG. 1 is a sectional view of the first embodiment of present invention. At first, powdered chitin 2 is coated on the water soluble polymer film 3. This chitin coated surface is an applying surface of the protective material 1. The water soluble polymer used in this embodiment is a natural, neutral multi-saccharide, quickly dissolves in cold and hot water, has a low viscosity when compared with other multi-saccharides, and does not easily deteriorate. Furthermore, the polymer has superior adhesivity, coatability and membrane-forming properties. This natural, neutral multi-saccharide used in this embodiment is preferably Pluran manufactured by Hayashibara Company, Ltd.

Pluran film 3 is made by coating Pluran solution on a plastic film, for example, a PET (polyethylene telephtelate), and drying. In the present invention, before the Pluran is completely dried, powdered chitin 2 is uniformly coated by spraying or the like method, and the surface then dried.

In this embodiment, the chitin is coated in a powder form. Furthermore, in the case of a dried Pluran film, after applying steam to the surface of the Pluran film, powdered chitin can be coated on the surface.

Powdered chitin 2 is coated on the plastic film and dried and the Pluran film 3 is made by tearing a plastic film, such as PET, off. A body fluid absorbing layer 4, such as a compressed cotton, cellulose sponge, absorbent non-woven fabric, etc., is provided on the back surface of the Pluran film 3. Furthermore, a sheet form tape material 6 is adhered to a back surface of the body fluid absorbing layer 4 by an acrylic or silicone or the like adhesive layer 5.

Figure 2:
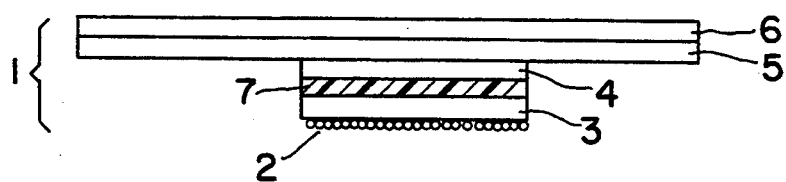
FIG. 2 is an enlarged sectional view of an improved embodiment of FIG. 1.
Figure 3:
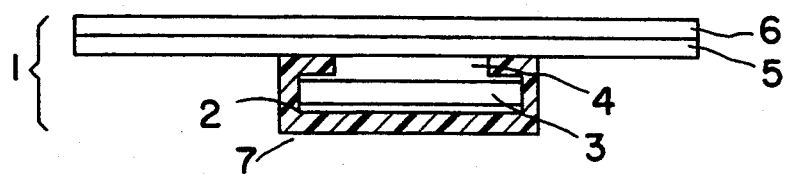
FIG. 3 is another enlarged sectional view of the improved embodiment of FIG. 1.

In order to protect the Pluran layer 3 and the chitin layer 2 and to accelerate tearing off of the protective material 1, it is preferable that a water insoluble net 7, such as a polyethylene net, be provided between the Pluran film 3 and body fluid absorbing layer 4 (FIG. 2), and/or outer surface of the chitin powder layer 2 (FIG. 3).

One of the characteristics of this wound surface protective applying material is that chitin exists in a powder form. Since a water soluble polymer (blood soluble) is used as a binder, and a body fluid absorbing material is provided, each effect is synergistically shown. In the case of tearing off of the protective material, only the powdered chitin remains on the wound surface. As a result, the wound surface is not injured and tearing off is possible without pain.

Embodiment 2

Figure 4:
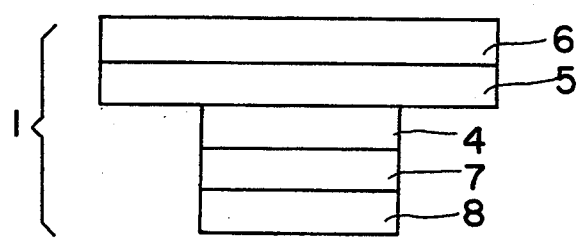
FIG. 4 is an enlarged sectional view of a second embodiment of a wound surface protective material according to the present invention.

FIG. 4 is a sectional view of another embodiment of the applying material 1, for protecting a wound surface. Powdered chitin is uniformly distributed in a solution of a water soluble polymer (for example, Pluran manufactured by Hayashibara Company, Ltd.), and the liquid is formed in a film form 8. The Pluran is the same as is used in the embodiment shown in FIG. 1. The film is used as the applying member of the applying material for protecting a wound surface.

In this embodiment, a body fluid absorbing material layer 4, such as compressed cotton, cellulose sponge or non-woven fabric, is provided on the back surface of the Pluran film 8 in which the chitin powder is mixed and dispersed. Furthermore, a tape material 6 for adhering to the skin is adhered to a back surface of the body fluid absorbing material layer 4 by an acrylic or silicone adhesive layer 5 and the like.

Figure 5:
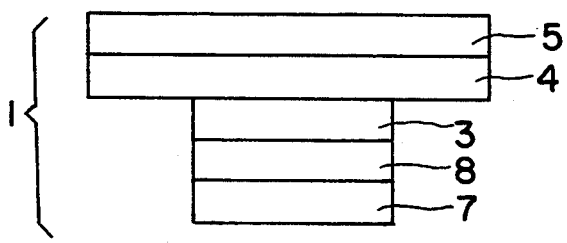
FIG. 5 is an enlarged sectional view of the embodiment in FIG. 4.

In order to protect the Pluran film 8 in which the chitin powder is mixed and dispersed and to accelerate the tearing off of the applying material, it is preferable that a water insoluble net 7 be provided between the Pluran film 8 and body fluid absorbing layer 4 (FIG. 4 and FIG. 6), and/or outer surface of the Pluran film 8 (FIG. 5).

Figure 6:
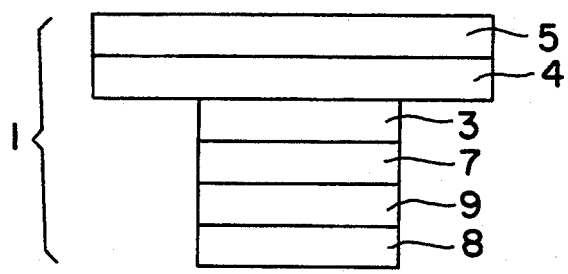
FIG. 6 is another enlarged sectional view of the embodiment in FIG. 4.

In the water soluble film including chitin, the quantity of chitin powder mixed in is less than 50% by dry weight. If the quantity is too much, the strength of the film including the chitin powder may deteriorate. In this case, in order to reinforce the film, a Pluran film including no chitin powder 9 may be provided as shown in FIG. 6.

One of the characteristics of this wound surface protective applying material is that the chitin is formed in a powder form. Furthermore, since a water soluble polymer (blood soluble) is used as a binder, and a body fluid absorbing material is provided, each effect is synergistically shown. In case of tearing off of the protective material, only the powdered chitin remains on the wound surface. As a result, the wound surface is not injured and tearing off of the protective material is possible without pain.

Embodiment 3

Figure 7:
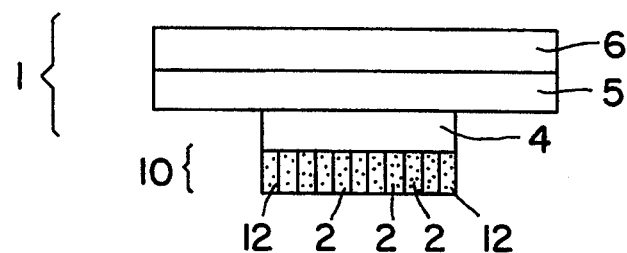
FIG. 7 is an enlarged sectional view of a third embodiment of a wound surface protective material according to the present invention.

FIG. 7 is a sectional view of another embodiment of the applying material for protecting a wound surface according to the present invention. Powdered chitin is uniformly dispersed in a solution of a water soluble polymer (Pluran manufactured by Hayashibara Company, Ltd,), and a net 12 is soaked in the liquid and dried. This net 12 having powdered chitin is an applying surface 10 of the protective material 1. A body fluid absorbing material 4, such as compressed cotton, cellulose sponge or a non-woven fabric, is provided on the back surface of the net 12. Furthermore, a tape material 6 for adhering to the skin is adhered on the back surface of the body fluid absorbing material layer 4 by an acrylic or siliconic adhesive layer 5 or the like.

Knitted, textured or non-woven fabric, using natural or synthetic fibers (polyethylene, polyamide, cotton, rayon and the like) can be used as a net 12 to be fixed to the powdered chitin 2. While fixing by soaking is difficult because of the high shedding property of the net 12, the viscosity of the water soluble polymer (Pluran) may be made higher and the polymer liquid may be pushed out or coated on the net and dried.

One of the characteristics of this wound surface protective applying material is that the chitin powder directly contacts the wound surface in a dispersion state to improve the treatment effect. Furthermore, since the quantity of Pluran is reduced by using a net, the flexibility of the applying material can be maintained. Still further, in this embodiment, since the chitin powder is dispersed in a water soluble binder which is dissolved by body fluid and is fixed to the net, the powder does not come off the net during the distribution of the goods. Also, when the applying material is applied to the wound surface, the binder is dissolved by the body fluid to thereby make it possible to be torn off without pain. Also, the quantity of Pluran can be reduced since a flexible net is used.

Embodiment 4

Figure 8:
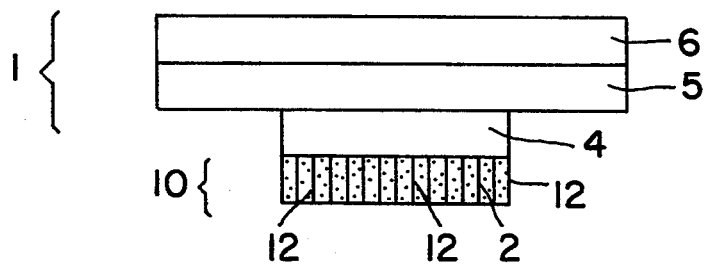
FIG. 8 is an enlarged sectional view of a fourth embodiment of a wound surface protective material according to the present invention.

FIG. 8 is a sectional view of another embodiment of the applying material 1 for protecting a wound surface according to the present invention. The powdered chitin is uniformly dispersed in a water or a solution which has less surface tension than water, such as ethanol and isopropyl alcohol. A proper quantity, that is less than 20% of powdered chitin (preferably 1 to 10%) of water holding agent, such as a solution in which a water soluble and a non-volatile compound (glycerin or the like) is dissolved, is coated on the net 12 by gravure coating or reverse coating, and dried. The net 12 on which chitin powder 2 is fixed is an applying surface 10 of the applying material 1.

As discussed above, powdered chitin is fixed on the net 12 by coating and drying; but it does not crack, and the initial applied condition is maintained after drying as a result of using the water holding agent. A body fluid absorbing material layer 4, such as compressed cotton, cellulose sponge or non-woven fabric, is adhered onto the back surface of the net 12 on which chitin powder is fixed. Furthermore, a tape material 6 is adhered to the body fluid absorbing material layer 4 by an acrylic or siliconic adhesive 5.

Knitted, textured or non-woven fabric using natural or synthetic fibers (polyethylene, polyamide, cotton, rayon and the like) can be used as the net 12 to which the powdered chitin 2 is fixed.

The solvent or dispersion liquid which is coated on the net 12 or in which the net 12 is dipped may be water, but a solution which has less surface tension than water, such as ethanol or isopropyl alcohol, is preferable. By using such a liquid, the dispersion and the coating are more uniform to thereby improve the adhesivity. Still further, in this embodiment, if a water holding agent such as glycerin is not used, coating on the net is possible, but the glycerin prevents the chitin from coming off the net after drying.

In this embodiment, the net 12 on which the chitin powder is dispersed uniformly together with water holding agent in water or low surface tension solution and then coated and dried, is the applying surface 10 for the applying material 1 for protecting a wound surface. As a result, the chitin is fixed without another binder, but the chitin powder does not come off the net during distribution of the goods as a result of the effect of the water holding agent. When applied on a wound surface, the chitin powder easily contacts and moves to the wound; and when being torn off, it tears off without pain and aggravation of the wound.

We claim:

1. An applying material for protecting a wound surface comprising:
    a film of a water soluble polymer,
    a powdered chitin coated on said film,
    a body fluid absorbing layer selected from the group consisting of compressed cotton, cellulose sponge and non-woven texture provided on a back surface of said film, and
    a tape material adhered on said body fluid absorbing layer by adhesive.

2. An applying material for protecting a wound surface as set forth in claim 1, wherein said water soluble polymer film is made by coating a water soluble polymer solution on a plastic film and spraying powdered chitin on it before drying the polymer.

3. An applying material for protecting a wound surface as set forth in claim 1, wherein said water soluble polymer film is made by steaming the film of the water soluble polymer and coating the powdered chitin thereon before drying the steam.

4. An applying material for protecting a wound surface as set forth in claim 1, wherein a water insoluble net is provided between said water soluble polymer film and body fluid absorbing layer.

* * * * *